United States Patent [19]

Müller-Rees et al.

[11] Patent Number: 5,851,277
[45] Date of Patent: Dec. 22, 1998

[54] PREPARATION WHOSE COLORING DEPENDS ON THE VIEWING ANGLE

[75] Inventors: Christoph Müller-Rees, Pullach; Annemarie Huber, Haiming, both of Germany

[73] Assignee: Wacker-Chemie GmbH, Germany

[21] Appl. No.: 889,343

[22] Filed: Jul. 8, 1997

[30] Foreign Application Priority Data

Jul. 23, 1996 [DE] Germany ............... 196 29 761.2

[51] Int. Cl.$^6$ ................ A61K 47/30; C09K 19/02
[52] U.S. Cl. ............. 106/287.35; 106/266; 106/272; 106/287.16; 514/772; 514/772.3
[58] Field of Search ............... 106/287.16, 493, 106/499, 500, 505, 506, 266, 272, 287.35; 528/502; 252/299.5; 514/772, 772.3

[56] References Cited

U.S. PATENT DOCUMENTS

| | | |
|---|---|---|
| 3,711,308 | 1/1973 | Brand et al. . |
| 3,874,890 | 4/1975 | Bernhard et al. . |
| 3,926,659 | 12/1975 | Bernhard et al. . |
| 5,362,315 | 11/1994 | Müller-Rees et al. . |
| 5,364,557 | 11/1994 | Faris ................ 252/299.01 |

FOREIGN PATENT DOCUMENTS

| | | |
|---|---|---|
| 0383376 | 8/1990 | European Pat. Off. . |
| 0601483 | 6/1994 | European Pat. Off. . |
| 0686674 | 12/1995 | European Pat. Off. . |
| 1959998 | 7/1971 | Germany . |
| 2244298 | 3/1974 | Germany . |
| 2313331 | 9/1974 | Germany . |
| 2 282 146 | 3/1995 | United Kingdom . |

OTHER PUBLICATIONS

U.S. application No. 08/432,298, Müller–Rees et al., filed May 1, 1995.

*Primary Examiner*—David Brunsman
*Attorney, Agent, or Firm*—Brooks & Kushman P.C.

[57] ABSTRACT

The invention relates to cosmetic or pharmaceutical preparations comprising pigments whose coloring depends on the viewing angle and comprising additives which are customary for cosmetic or pharmaceutical preparations, wherein the pigments comprise at least one oriented crosslinked substance having a liquid-crystalline structure with a chiral phase, are plateletlike in form and have a thickness of 1–20 μm.

9 Claims, No Drawings

PREPARATION WHOSE COLORING DEPENDS ON THE VIEWING ANGLE

BRIEF SUMMARY OF THE INVENTION

The present invention relates to preparations whose coloring depends on the viewing angle.

BACKGROUND OF THE INVENTION

Cosmetic and/or pharmaceutical preparations, for example those for treating hair, nails and skin and containing pigments, are already widely known. In many cases there is a need for special-effect pigments which give the preparations a metallic colored luster and which comprise physiologically unobjectionable colorants which are approved in cosmetics.

It is known to use platelet-shaped pigments such as the metal oxide/mica pigments described in the patents U.S. Pat. No. 3,711,308 (corresponding to DE-A 19 59 998), U.S. Pat. No. 3,874,890 (corresponding to DE-A-22 44 298) and U.S. Pat. No. 3,926,659 (corresponding to DE-A-23 13 331). These pigments comprise thin mica flakes that are coated with iron oxide and in some cases with other metal oxides. These mica pigments feature countless very small metal oxide crystals, deposited alongside one another on the mica surface, and therefore possess—viewed microscopically—a relatively rough surface.

U.S. Pat. No. 5,362,315 (corresponding to EP-A-601 483) and EP-A-686 674 disclose pigments whose color depends on the viewing angle. In EP-A-686 674, it is mentioned that these pigments are suitable, among numerous other applications, for use in the cosmetics field, although further details on this are lacking.

DETAILED DESCRIPTION OF THE INVENTION

The object of the present invention was to provide cosmetic or pharmaceutical preparations which exhibit a high luster and color effects which are dependent on the viewing angle and which possess a very good feel on the skin.

The present invention provides cosmetic or pharmaceutical preparations comprising pigments whose coloring depends on the viewing angle and also comprising the additives which are customary for cosmetic or pharmaceutical preparations, wherein the pigments comprise at least one oriented crosslinked substance having a liquid-crystalline structure with a chiral phase, are platelet-like in form and have a thickness of 1–20 $\mu$m.

The pigments have a thickness of 4–8 $\mu$m, preferably from 4 to 6 $\mu$m.

The pigments have a particle diameter of 5–500 $\mu$m, preferably from 10 to 100 $\mu$m.

The novel preparations are environmentally friendly owing to the avoidance of pigments containing heavy metals.

The pigments present in the novel preparations are prepared as described, for example, in U.S. Pat No. 5,362,315 (corresponding to EP-A-601 483) or in EP-A-686 674, with the difference that, when the materials are comminuted to give the pigments, the above mentioned criteria in respect of form, thickness and, optionally, particle diameter are observed or the corresponding particles are selected, after having been comminuted, by means of known techniques such as, for example, classification. The teachings of U.S. Pat. No. 5,362,315 and EP-A-686 674 are incorporated herein by reference.

The pigments are present in the novel compositions in amounts of 0.05–40% (w/w), preferably 0.1–20% (w/w), more preferably 1–5% (w/w).

The pigments used in accordance with the invention preferably consist of polyorganosiloxanes.

It has been found that the novel preparations possess high gloss, diverse color effects which have depth and are, in particular, dependent on the viewing angle, and also, quite unexpectedly, a very good feel on the skin and pronounced absorption in the UV region. The novel formulations are easier to prepare than known cosmetic or pharmaceutical preparations, since the pigments whose coloring depends on the viewing angle are incorporated more readily into the respective formulations than are the customary pigments.

The novel preparations can be prepared by means of known and customary techniques. The pigments specified can be incorporated in a customary manner.

The novel compositions may, for example, comprise preparations for the treatment of skin, nails and hair. Examples are emulsions, such as cleansing emulsions, liquid nutrient creams, body lotions, sun protection products and bathing lotion, creams, for instance solid creams in the manner of a night cream, skin nutrient creams, sunscreen creams and the like, and also sticks, such as deodorant sticks, lipsticks and eye makeup sticks. The materials used are known to the skilled worker or can be found in standard works.

Examples of additives which may be present in the compositions are animal, mineral, vegetable or synthetic oils, waxes or resins, wetting agents, fatty alcohols, emulsifiers, sunscreens, organic solvents, thickeners, dyes, pigments, pH regulators, reducing agents, electrolytes, opacifying additives, preservatives, antioxidants, ion exchangers, fragrances, antiseborrheic agents and active substances which may serve to treat, care for and protect the skin or hair, and also water.

The nature and quantity of the additives depend on the particular field of application and are known in the area of cosmetology.

As coloring constituents the novel preparations always comprise at least one of the above mentioned platelet-shaped pigments whose coloring depends on the viewing angle. In addition, however, it is possible to mix in further pigments, it being possible to use both organic and inorganic absorption color pigments, silvery luster pigments, for example bismuth oxychloride, pearl essence or titanium dioxide-coated mica or interference color luster pigments based on mica flakes coated with metal oxides, especially $TiO_2$.

Highly appealing color effects are obtained by combining interference color pigments or metal luster pigments; consequently, such pigments are preferably present in the novel preparation.

The present invention therefore provides novel cosmetic preparations having attractive color effects and a very pleasant feel on the skin.

In the examples below, all parts and percentages are by weight unless stated otherwise. Furthermore, all viscosities relate to a temperature of 25° C. Unless stated otherwise, the examples which follow were conducted at the pressure of the surrounding atmosphere, i.e. at about 1000 hPa, and at room temperature, i.e. at about 20° C., or at the temperature which is established when the reactants are combined at room temperature without additional heating or cooling.

The novel formulations were prepared in accordance with methods customary in the cosmetics industry and using common raw materials.

The formulation samples were assessed by two or three individuals, the appearance and application being assessed subjectively.

EXAMPLE 1

Face Powder 70.00% of talc, 6.00% of magnesium stearate and 3.00% of acrylic polymer obtainable from Goodrich under the designation Carbopol 1342 were mixed, and 12.00% of a highly volatile cyclic polydimethylsiloxane obtainable commercially from Wacker-Chemie, Munich, under the designation Wacker-Belsil CM 040, and 2.00% of protein hydrolysate, obtainable commercially from Grünau under the designation Nutrilan L, were mixed in in portions. Then 0.20% of methylparaben, 1.90% of talc, 0.90% of color pigments consisting of 2 parts of Tudor Mahogany, 4 parts of Tudor Aspen, 3 parts of Tudor Rosewood, 6 parts of Tudor Willow, obtainable from Croda Nettetal; and 4.00% of platelet-shaped pigments whose coloring depends on the viewing angle were then mixed in, and all of the components were mixed homogeneously.

The platelet-shaped pigments whose coloring depends on the viewing angle were prepared as described in Example 3 of EP-A-686 674, with the difference that the layer thickness is 5 μm instead of 7 μm and that the pigment fraction used was obtained by milling for four minutes in a universal mill and then by screening with an analytical sieve having a mesh size of 50 μm.

It is possible optionally to add fragrances in an amount of from 0.1% to 1% (obtainable, for example, from Orissa Drebing, Hamburg).

The face powder produces a slightly glistening bronze effect on the skin with a pronounced color shading changing from red to green and a very good feel on the skin.

EXAMPLE 2

Mascara

Fraction A)
  5.00% of a waxlike siloxane containing stearyl groups, obtainable under the designation Wacker-Belsil SM 6018 from Wacker-Chemie, Munich
  4.00% of a polydimethylsiloxane containing phenyl groups, obtainable under the designation Wacker-Belsil PDM 200 from Wacker-Chemie, Munich
  5.00% of cetyl alcohol
  7.00% of stearic acid
  3.50% of vaseline
  4.50% of thick liquid paraffin.
Fraction B)
  0.90% of triethanolamine
  65.10% of water
Fraction C)
  3.00% of pigment colorant, for example Tudor Ebony from BASF
Fraction D)
  2.00% of platelet-shaped pigments whose coloring depends on the viewing angle (particle diameter 10 to 70 μm)

The platelet-shaped pigments whose coloring depends on the viewing angle were prepared as described in Example 4 of EP-A-686 674, with the difference that the layer thickness is 5 μm instead of 7 μm and that the pigment fraction used was obtained by milling for four minutes in a universal mill and then by screening with an analytical sieve having a mesh size of 66 μm.

Fraction A was melted at 60° C., Fraction B was mixed in with rapid stirring, and then Fraction C was incorporated homogeneously and Fraction D was mixed in subsequently.

The mascara was creamy and black with a greenish shimmer and a color flop from green to blue.

EXAMPLE 3

Mascara

The mascara was prepared as described in Example 2 with the exception that different platelet-shaped pigments whose coloring depends on the viewing angle were used, in a concentration of 3% instead of 2%.

The platelet-shaped pigments used in this example, whose coloring depends on the viewing angle, were prepared as described in Example 3 of EP-A-686 674, with the difference that the layer thickness is 5 μm instead of 7 μm, and the pigment fraction used was obtained by milling for four minutes in a universal mill and then screening with an analytical sieve having a mesh size of 66 μm.

The mascara was creamy and black with a red-gold shimmer and a color flop to green which was more pronounced than the color flop described in Example 2.

EXAMPLE 4

Lipstick 2.00% beeswax
  6.00% carnauba wax
  5.50% of candelilla wax
  6.50% of ozokerite
  1.50% of microcrystalline wax
  5.50% of thick liquid paraffin
  3.00% of vaseline
  5.00% of a waxlike siloxane containing stearyl groups, obtainable under the designation Wacker-Belsil SM 6018 from Wacker-Chemie, Munich
  15.00% of lanolin oil obtainable from Grünau under the designation Fluilan
  35.00% of castor oil
  5.00% of superfatting agent obtainable, for example, from Goldschmidt under the designation Tegosoft 189
  3.00% of a polydimethylsiloxane containing phenyl groups, obtainable under the designation Wacker-Belsil PDM 1000 from Wacker-Chemie, Munich
  4.00% of color pigment obtainable from BASF under the designation Sicomet Red 30
  3.00% of platelet-shaped pigments whose coloring depends on the viewing angle (particle diameter 8–30 μm).

The platelet-shaped pigments used in this example, with their coloring dependent on the viewing angle, were prepared as described in Example 3 of EP-A-686 674, with the difference that the layer thickness is 5 μm instead of 7 μm, and the pigment fraction used was obtained by milling for seven minutes in a universal mill and then screening with an analytical sieve having a mesh size of 25 μm.

All of the components were mixed and melted together.

The lipstick glistens slightly and on the skin gives moderate color effects with a color flop from red to gold.

EXAMPLE 5

Lipstick

The lipstick was prepared as described in Example 4 with the difference that the color pigment used was Sicomet Red 15850 Ca, obtainable from BASF, and that different platelet-shaped pigments whose coloring depends on he viewing angle were used.

The platelet-shaped pigments used in this example, with their coloring dependent on the viewing angle, were prepared as described in Example 4 of EP-A-686 674, with the difference that the layer thickness is 5 μm instead of 7 μm, and the pigment fraction used was obtained by milling for seven minutes in a universal mill and then screening with an analytical sieve having a mesh size of 25 μm.

The lipstick has a greenish shimmer and on the skin gives moderate color effects with a color flop from orange to lilac.

EXAMPLE 6

Hair Gel

Fraction A)
- 1.20% of acrylamide/acrylate copolymer obtainable from Hoechst under the designation Hostacerin PN 73
- 1.20% of polyvinylpyrrolidone obtainable, for example, from BASF under the designation Luviskol VA 64

Fraction B)
- 20.00% of isopropanol
- 2.00% of polydimethylsiloxane containing phenyl groups, obtainable under the designation Wacker-Belsil PDM 20 from Wacker-Chemie, Munich
- 71.60% of water Fraction C)
- 4.00% of platelet-shaped pigments whose coloring depends on the viewing angle (particle diameter 30–100 μm)

The platelet-shaped pigments used in this case whose coloring depends on the viewing angle were prepared as described in Example 4 of EP-A-686 674, the layer thickness being 5 μm instead of 7 μm and the pigment fraction used being obtained by milling for three minutes in a universal mill and then screening with an analytical sieve having a mesh size of 100 μm and screening the resulting sieve fraction with a second analytical sieve having a mesh size of 32 μm, as oversize.

Fraction B was mixed, Fraction A was slowly mixed into Fraction B, and then Fraction C was mixed in.

The hair gel has a greenish shimmer in the glass container and on the skin and in black hair provides strong effects with a color flop from green to blue; in light-colored hair, the effects are somewhat more moderate.

EXAMPLE 7

Self-Foaming Lotion

Fraction A)
- 81.50% of water
- 1.00% of acrylic acid polymer, obtainable for example from B. F. Goodrich under the designation Carbopol 934
- 2.50% of vinyl acetate/ethylene copolymer, under the designation Vinnapas RE 526-Z from Wacker-Chemie, Munich Fraction B)
- 1.00% of triethanolamine Fraction C)
- 2.50% of sodium lauryl sulfate, obtainable for example under the designation Texapon N 40 from Henkel, Düsseldorf
- 9.00% of low-viscosity volatile polydimethylsilox ane, obtainable under the designation Wacker-Belsil DM 0.65 from Wacker-Chemie, Munich
- 0.50% of glucose-functional polydimethylsiloxane obtainable under the designation SPG 121 VP from Wacker-Chemie, Munich
- 2.00% of platelet-shaped pigments whose coloring depends on the viewing angle (particle diameter 20 to 260 μm).

The platelet-shaped pigments used, whose coloring depends on the viewing angle, were prepared as described in Example 3 of EP-A-686 674, with the difference that the layer thickness is 5 μm instead of 7 μm, and the pigment fraction used was obtained by milling for two minutes in a universal mill and then screening with an analytical sieve having a mesh size of 250 μm.

Fraction A was mixed thoroughly until a homogeneous solution had formed, which was then neutralized with Fraction B, and Fraction C was mixed in.

The self-foaming lotion is highly glistening and, on the skin, exhibits a particularly strongly pronounced red-green color flop effect.

EXAMPLE 8

Sunscreen Lotion

Fraction A)
- 6.00% of emulsifier mixture obtainable commercially, for example, under the designation Teginacid from Goldschmidt
- 1.00% of isopropyl myristate
- 1.00% of polydimethylsiloxane obtainable under the designation Wacker-Belsil DM 350 from Wacker-Chemie, Munich
- 4.00% of thin liquid paraffin
- 1.00% of cetyl stearyl alcohol, obtainable for example under the designation Lanette O from Henkel, Düsseldorf Fraction B)
- 10.00% of a combination of a highly viscous poly dimethylsilicone rubber with highly volatile cyclic polydimethylsiloxanes, obtainable under the designation Wacker-Belsil CM 1000 from Wacker-Chemie, Munich
- 2.00% of UV absorber, obtainable for example from Givaudan-Roure under the designation Parsol MCX Fraction C)
- 71.50% of water
- 1.50% of glycerol Fraction D)
- 2.00% of platelet-shaped pigments whose coloring depends on the viewing angle (particle size 10–55 μm).

The platelet-shaped pigments used here, whose coloring depends on the viewing angle, were prepared as described in Example 4 B of EP-A-686 674, with the difference that, the pigment fraction used was obtained by milling for five minutes in a universal mill and then screening with an analytical sieve having a mesh size of 50 μm.

Fraction A and Fraction C were each heated to 65°–70° C. Fraction C was stirred into Fraction A, and then Fraction B was mixed in at about 40° C. Fraction D was incorporated homogeneously into the finished formulation.

The sunscreen lotion shows moderate color effects on skin with a color flop from green to blue.

EXAMPLE 9

Sunscreen Stick

Fraction A)
- 67.00% of vaseline
- 25.00% of stearoxy-functional waxlike polydimethyl siloxane, obtainable under the designation Wacker-Belsil SDM 6022 from Wacker-Chemie, Munich Fraction B)
- 4.00% of UV absorber obtainable, for example, under the designation Parsol MCX from Givaudan-Roure
- 4.00% of platelet-shaped pigments whose coloring depends on the viewing angle (particle diameter 10 to 55 μm).

The platelet-shaped pigments used, whose coloring depends on the viewing angle, were prepared as described in Example 3 of EP-A-686 674, with the difference that the layer thickness is 5 μm instead of 7 μm, and the pigment fraction used was obtained by milling for five minutes in a universal mill and then screening with an analytical sieve having a mesh size of 50 μm.

Fraction A was heated to about 60° C. and mixed thoroughly, and Fraction B was mixed in at about 40° C. The mixture was then introduced into the mold.

The sunscreen stick shows attractive bronze effects on the skin with a color flop from red to green. In the region of UV-C (200–230 nm) and UV-B (290–330 nm) radiation, increased absorption was found in comparison to the formulation without platelet-shaped pigments whose coloring depends on the viewing angle.

EXAMPLE 10

Sunscreen Stick

Fraction A)
- 62.00% of vaseline
- 30.00% of stearoxy-functional waxlike polydimethyl siloxane, obtainable under the designation Wacker-Belsil SDM 6022 from Wacker-Chemie, Munich Fraction B)
- 4.00% of UV absorber obtainable, for example, under the designation Parsol MCX from Givaudan-Roure
- 4.00% of platelet-shaped pigments whose coloring depends on the viewing angle (particle diameter 10 to 50 μm).

The platelet-shaped pigments used, whose coloring depends on the viewing angle, were prepared as described in Example 4 of EP-A-686 674, with the difference that the layer thickness is 5 μm instead of 7 μm, and the pigment fraction used was obtained by milling for five minutes in a universal mill and then screening with an analytical sieve having a mesh size of 50 μm.

Fraction A was heated to about 60° C. and mixed thoroughly and then cooled, and Fraction B was mixed in at about 40° C. The mixture was then introduced into the mold.

The sunscreen stick is a soft stick which in the packaging has a slight greenish shimmer and on the skin shows a color flop to blue. It is ideal as a lipcare stick with sunscreen.

EXAMPLE 11

Colorless Nail Varnish

Fraction A)
- 18.00% of nitrocellulose, obtainable commercially, for example, from ICI, Frankfurt
- 4.00% of silsesquioxane containing phenyl groups, obtainable from Wacker-Chemie, Munich under the designation Intermediate SY 430,
- 11.00% of xylene
- 5.00% of methyl ethyl ketone
- 22.00% of ethyl acetate
- 22.00% of butyl acetate Fraction B)
- 2.00% of camphor
- 3.00% of butyl glycolate
- 1.00% of diisopropyl adipate, obtainable commercially, for example, from Dragoco, Holzminden under the designation Isoadipat
- 8.00% of ethanol
- 2.00% of dibutyl phthalate Fraction C)
- 2.00% of platelet-shaped pigments whose coloring depends one the viewing angle (particle diameter 100 to 260 nm).

The platelet-shaped pigments used whose coloring depends on the viewing angle were prepared as described in Example 4 of EP-A-686 674, with the difference that the layer thickness is 5 μm instead of 7 μm, and the pigment fraction used was obtained by milling for two minutes in a universal mill and then screening using an analytical sieve having a mesh size of 250 μm and then a second screening of the sieved material through an analytical sieve having a mesh size of 100 μm, as oversize.

Fraction A was mixed thoroughly and stirred until a homogeneous mixture had formed. Fraction B was mixed in homogeneously and then Fraction C was added.

The colorless nail varnish gives attractive color effects with a color flop from green to blue, which is intensified further when it is applied over a dark under varnish.

EXAMPLE 12

Eyeshadow Compact Powder

Fraction A)
- 20.00% of talc
- 25.00% of kaolin
- 5.00% of titanium dioxide
- 10.00% of calcium carbonate
- 5.00% of magnesium stearate
- 5.00% of boron nitride, obtainable under the designation Wacker Bornitrid BNP from Wacker-Chemie, Munich
- 12.50% of zinc stearate Fraction B)
- 3.50% of isopropyl myristate
- 4.00% of oleyl oleate, obtainable for example under the designation Cetiol from Henkel, Dusseldorf Fraction C)
- 5.00% of platelet-shaped pigments whose coloring depends on the viewing angle (particle diameter 5–35 μm)
- 5.00% of pigment dye obtainable, for example, under the designation Cloisonne Blue 650 Z from Mearl The platelet-shaped pigments used whose coloring depends on the viewing angle were prepared as described in Example 4 of EP-A-686 674 with the difference that the layer thickness is 5 μm instead of 7 μm, and the pigment fraction used was obtained by milling for seven minutes in a universal mill and then screening using an analytical sieve having a mesh size of 32 μm.

Mix Fraction A thoroughly, heat Fraction B and mix it in portions, mix in Fraction C and homogenize the mixture well, and then press it to form small blocks.

The eyeshadow compact powder is a lilac powder with a slightly greenish shimmer and a color flop to blue.

EXAMPLE 13

Shower Gel 22.50% of alkylamidopropylbetain, obtainable for example from Hoechst under the designation Genagen CAB 53.50% of water 22.50% of ammonium lauryl ether sulfate, obtainable for example from Henkel, Düsseldorf under the designation Texapon NA 1.00% of polyether-modified polydimethylsiloxane, obtainable from Wacker-Chemie under the designation Wacker-Belsil DMC 6038

0.50% of ammonium chloride 2.00% of platelet-shaped pigments whose coloring depends on the viewing angle (particle diameter 50 to 260 µm)

The platelet-shaped pigments used whose coloring depends on the viewing angle were prepared as described in Example 4 of EP-A-686 674, with the difference that the layer thickness is 5 µm instead of 7 µm, and the pigment fraction used was obtained by milling for three minutes in a universal mill and then screening using an analytical sieve having a mesh size of 250 µm and then a second screening of the sieved material through an analytical sieve having a mesh size of 50 µm, as oversize.

All of the components were mixed in the sequence given.

The shower gel has a marked greenish shimmer and shows a strong color flop to blue.

EXAMPLE 14

Shower Gel

The shower gel was prepared as described in Example 13 with the difference that 0.2% of platelet-shaped pigments whose coloring depends on the viewing angle were employed.

In comparison with the shower gel from Example 13, the shower gel has a less pronounced greenish shimmer and showed a highly moderate color flop to blue.

EXAMPLE 15

Body Gel

Fraction A)

0.40% of an acrylic acid polymer obtainable commercially, for example, from B. F. Goodrich under the designation Carbopol 94, 64.70% of water.

Fraction B)

0.80% of a polyether-modified polydimethylsiloxane, obtainable commercially from Wacker-Chemie, Munich under the designation Wacker-Belsil DMC 6031

Fraction C)

33.00% of ethanol

Fraction D)

0.30% of triethanolamine

Fraction E)

0.05% of pigments whose coloring depends on the viewing angle, as used in Example 10.

Fraction A was mixed thoroughly and heated to 75° C., Fraction B was mixed in, and the mixture was stirred thoroughly. After cooling to about 45° C., Fraction C and then Fraction D were mixed in.

The body gel had a greenish blue shimmer. It is outstandingly suitable as a gel base for medical gels.

EXAMPLE 16

Ointment Base

Fraction A)

9.00% of cetyl stearyl alcohol, obtainable for example from Henkel, Düsseldorf under the designation Lanette O 10.50% of thick liquid paraffin 10.50% of white vaseline 1.00% of polydimethylsiloxane with a viscosity of 350 mm²/s, obtainable from Wacker-Chemie, Munich under the designation Pharsil 350

Fraction B)

68.00% of water

Fraction C)

1.00% of pigments whose coloring depends on the viewing angle, as used in Example 10.

Fraction A was heated to about 65°–70° C. Fraction B was heated and mixed into Fraction A, and the mixture was homogenized thoroughly. Then Fraction C was mixed in homogeneously.

The resulting ointment base had a greenish blue shimmer and was used as a creamy base for the incorporation of pharmaceutical active substances with an appealing appearance and an outstanding feel on the skin.

EXAMPLE 17

Toothpaste 19.00% of water were introduced and 0.50% of sodium carboxymethylcellulose, obtainable for example from Hoechst under the designation Tylose CB 200, and also 5.70% of highly disperse silicic acid, obtainable under the designation HDK N 20 P from Wacker-Chemie, Munich, were added with stirring.

4.30% of polyethylene glycol 400, 17.00% of 70% sorbitol solution and 50.00% of glycerol were stirred in. 4.00% of pigment whose coloring depends on the viewing angle, as used in Example 11, 2.50% of sodium lauryl sulfate, obtainable for example under the designation Texapon K 1296 from Henkel, Düsseldorf were mixed in carefully. During this addition, severe foaming was avoided. The finished formulation was evacuated for a short time.

A transparent toothpaste was obtained with an interesting play of color from green to blue.

What is claimed is:

1. A cosmetic or pharmaceutical preparation comprising pigments whose coloring depends on the viewing angle and additives selected from the group consisting of additives acceptable for use in cosmetic and pharmaceutical preparations, wherein the pigments comprise at least one oriented crosslinked substance having a liquid-crystalline structure with a chiral phase, are plateletlike in form, have a thickness of 1–20 µm, and a particle diameter of 5–500 µm.

2. A preparation as claimed in claim 1, wherein the pigments have a thickness of 4–8 µm.

3. A preparation as claimed in claim 1, wherein the pigments have a thickness of 4–6 µm.

4. A preparation as claimed in claim 1, wherein the pigments have a particle diameter of 10–100 µm.

5. A preparation as claimed in claim 1, wherein the pigments are present in the novel composition in amounts of 0.05–40% (w/w).

6. A preparation as claimed in claim 1, wherein the pigments are present in the novel composition in amounts of 0.1–20% (w/w).

7. A preparation as claimed in claim 1, wherein the pigments consist of polyorganosiloxanes.

8. A preparation as claimed in claim 1, which additionally comprises interference color pigments or metal luster pigments.

9. A preparation as claimed in claim 1, wherein additives present are one or more substances selected from the group consisting of animal, mineral, vegetable or synthetic oils, waxes or resins, wetting agents, fatty alcohols, emulsifiers, sunscreens, organic solvents, thickeners, dyes, pigments, pH regulators, reducing agents, electrolytes, opacifying additives, preservatives, antioxidants, ion exchangers, fragrances, antiseborrheic agents and active substances which may serve to treat, care for and protect the skin or hair, and also water.

* * * * *